(12) United States Patent
Peters et al.

(10) Patent No.: US 7,910,578 B2
(45) Date of Patent: Mar. 22, 2011

(54) 8,10-DIAZA-BICYCLO[4.3.1]DECANE DERIVATIVES AND THEIR MEDICAL USE

(75) Inventors: Dan Peters, Malmö (SE); Gunnar M. Olsen, Smørum (DK); Elsebet Østergaard Nielsen, København K (DK); Daniel B. Timmermann, Herlev (DK); Steven Charles Loechel, Frederiksberg (DK); Jeppe Kejser Christensen, København N (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 239 days.

(21) Appl. No.: 12/298,290

(22) PCT Filed: May 21, 2007

(86) PCT No.: PCT/EP2007/054870
§ 371 (c)(1),
(2), (4) Date: Oct. 23, 2008

(87) PCT Pub. No.: WO2007/135121
PCT Pub. Date: Nov. 29, 2007

(65) Prior Publication Data
US 2009/0099153 A1    Apr. 16, 2009

(30) Foreign Application Priority Data

May 23, 2006 (DK) ................................. 2006 00706

(51) Int. Cl.
*C07D 487/08* (2006.01)
*A61K 31/551* (2006.01)

(52) U.S. Cl. ........................................ 514/221; 540/556

(58) Field of Classification Search ................ 514/221; 540/556
See application file for complete search history.

(56) References Cited

U.S. PATENT DOCUMENTS

| 5,478,939 A | 12/1995 | Trybulski et al. |
| 2003/0225268 A1 | 12/2003 | Bunnelle et al. |
| 2005/0101602 A1 | 5/2005 | Basha et al. |

FOREIGN PATENT DOCUMENTS

| WO | WO-00/66586 A1 | 11/2000 |
| WO | WO-01/90109 A1 | 11/2001 |
| WO | WO-01/92259 A1 | 12/2001 |
| WO | WO-01/92260 A1 | 12/2001 |
| WO | WO-01/92261 A1 | 12/2001 |
| WO | WO-02/02564 A1 | 1/2002 |
| WO | WO-03/004493 A1 | 1/2003 |
| WO | WO-2006/045716 A1 | 5/2006 |
| WO | WO-2006/087306 A2 | 8/2006 |
| WO | WO-2007/065892 A1 | 6/2007 |
| WO | WO-00/44755 A1 | 8/2008 |

*Primary Examiner* — Bruck Kifle
(74) *Attorney, Agent, or Firm* — Birch, Stewart, Kolasch & Birch, LLP

(57) ABSTRACT

This invention relates to novel 8,10-diaza-bicyclo[4.3.1]decane derivatives, which are found to be cholinergic ligands at the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

10 Claims, No Drawings

8,10-DIAZA-BICYCLO[4.3.1]DECANE DERIVATIVES AND THEIR MEDICAL USE

TECHNICAL FIELD

This invention relates to novel 8,10-diaza-bicyclo[4.3.1] decane derivatives, which are found to be cholinergic ligands at the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency.

SUMMARY OF THE INVENTION

The present invention is devoted to the provision novel modulators of the nicotinic receptors, which modulators are useful for the treatment of diseases or disorders related to the cholinergic receptors, and in particular the nicotinic acetylcholine receptor (nAChR).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel 8,10-diaza-bicyclo[4.3.1]-decane derivatives of Formula I

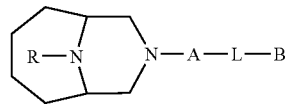

or a pharmaceutically acceptable salt thereof, wherein

A represents a mono- or bi-cyclic, carbocyclic or heterocyclic group;

L represents a single (covalent) bond (i.e. L is absent) or a linking group —C≡C—;

B represents a mono- or bi-cyclic, carbocyclic or heterocyclic group, which carbocyclic or heterocyclic group is optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl; and R represents hydrogen or alkyl.

In its second aspect the invention provides pharmaceutical compositions comprising a therapeutically effective amount of the 8,10-diaza-bicyclo[4.3.1]decane derivatives of the invention, or a pharmaceutically-acceptable addition salt thereof, or a prodrug thereof, together with at least one pharmaceutically-acceptable carrier or diluent.

In a further aspect the invention relates to the use of the 8,10-diaza-bicyclo[4.3.1]decane derivatives of the invention, or a pharmaceutically-acceptable addition salt thereof, for the manufacture of a pharmaceutical composition/-medicament for the treatment, prevention or alleviation of a disease or a disorder or a condition of a mammal, including a human, which disease, disorder or condition is responsive to modulation of cholinergic receptors.

In a final aspect the invention provides methods of treatment, prevention or alleviation of diseases, disorders or conditions of a living animal body, including a human, which disorder, disease or condition is responsive to modulation of cholinergic receptors, which method comprises the step of administering to such a living animal body in need thereof a therapeutically effective amount of the 8,10-diaza-bicyclo-[4.3.1]decane derivatives of the invention.

Other objects of the invention will be apparent to the person skilled in the art from the following detailed description and examples.

DETAILED DISCLOSURE OF THE INVENTION 8,10-Diaza-bicyclo[4.3.1]decane Derivatives In a first aspect novel 8,10-diaza-bicyclo[4.3.1]decane derivatives are provided. The 8,10-diaza-bicyclo[4.3.1]decane derivatives of the invention may be represented by the general Formula I

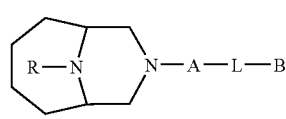

or a pharmaceutically acceptable salt thereof, wherein

A represents a mono- or bi-cyclic, carbocyclic or heterocyclic group;

L represents a single (covalent) bond (i.e. L is absent) or a linking group —C≡C—;

B represents a mono- or bi-cyclic, carbocyclic or heterocyclic group, which carbocyclic or heterocyclic group is optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl; and R represents hydrogen or alkyl.

In a first more preferred embodiment the 8,10-diaza-bicyclo[4.3.]decane derivative of the invention is a compound of Formula Ia

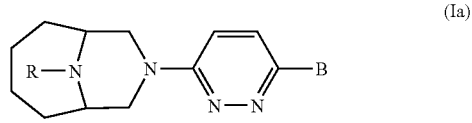

(Ia)

or a pharmaceutically acceptable salt thereof, wherein

B represents a mono- or bi-cyclic, carbocyclic or heterocyclic group, which carbocyclic or heterocyclic group is optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl; and R represents hydrogen or alkyl.

In a second more preferred embodiment the 8,10-diaza-bicyclo-[4.3.1]decane derivative of the invention is a compound of Formula Ib

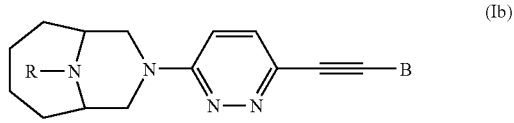

(Ib)

or a pharmaceutically acceptable salt thereof, wherein

B represents a mono- or bi-cyclic, carbocyclic or heterocyclic group, which carbocyclic or heterocyclic group is optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl; and R represents hydrogen or alkyl.

In a third more preferred embodiment the 8,10-diaza-bicyclo[4.3.1]decane derivative of the invention is a compound of Formula I, Ia or Ib, wherein L represents a single (covalent) bond (i.e. L is absent) or a linking group —C≡C—.

In a more preferred embodiment L represents a single (covalent) bond (i.e. L is absent).

In another more preferred embodiment L represents —C≡C—.

In a fourth more preferred embodiment the 8,10-diaza-bicyclo[4.3.1]decane derivative of the invention is a compound of Formula I, Ia or Ib, wherein A represents a mono- or bi-cyclic, carbocyclic or heterocyclic group.

In a more preferred embodiment A represents a monocyclic heterocyclic group selected from pyrazolyl, 1,3,4-oxadiazolyl, 1,3,4-thiadiazolyl, pyridinyl, pyridazinyl and pyrimidinyl.

In another more preferred embodiment A represents a pyridazinyl group.

In a fifth more preferred embodiment the 8,10-diaza-bicyclo[4.3.1]decane derivative of the invention is a compound of Formula I, Ia or Ib, wherein B represents a mono- or bi-cyclic, carbocyclic or heterocyclic group, which carbocyclic or heterocyclic group is optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl.

In a more preferred embodiment B represents a phenyl or thienyl group, optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl.

In an even more preferred embodiment B represents a phenyl or thienyl group, optionally substituted one or two times with alkyl, cycloalkyl, hydroxy, alkoxy, halo and/or trifluoromethyl.

In a still more preferred embodiment B represents phenyl or thienyl.

In another more preferred embodiment B represents a phenyl group, optionally substituted one or more times with alkyl, cycloalkyl, cycloalkyl-alkyl, hydroxy, alkoxy, halo, haloalkyl, haloalkoxy, cyano, nitro, amino, oxo, carboxy, alkyl-carbonyl, alkoxy-carbonyl, alkyl-carbonyl-oxy, carbamoyl, amido, sulfamoyl, phenyl and/or benzyl.

In an even more preferred embodiment B represents a phenyl group, optionally substituted one or two times with alkyl, cycloalkyl, hydroxy, alkoxy, halo and/or trifluoromethyl.

In a yet more preferred embodiment B represents phenyl.

In another yet more preferred embodiment B represents thienyl.

In a sixth more preferred embodiment the 8,10-diaza-bicyclo[4.3.1]decane derivative of the invention is a compound of Formula I, Ia or Ib, wherein R represents hydrogen or alkyl.

In a more preferred embodiment R represents hydrogen.

In another more preferred embodiment R represents alkyl, and in particular methyl.

In a most preferred embodiment the 8,10-diaza-bicyclo[4.3.1]decane derivative of the invention is 10-Methyl-8-(6-phenyl-pyridazin-3-yl)-8,10-diaza-bicyclo[4.3.1]decane; or 10-Methyl -8-(6-phenylethynyl-pyridazin-3-yl)-8,10-diaza -bicyclo[4.3.1]decane;

10-Methyl-8-(6-thiophen-3-yl-pyridazin-3-yl)-8,10-diaza -bicyclo[4.3.1]decane; or 10-Methyl-8-(6-thiophen-2-yl-pyridazin-3-yl)-8,10-diaza -bicyclo[4.3.1]decane;

or a pharmaceutically acceptable salt thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Preferred haloalkyl groups of the invention include trihalomethyl, preferably trifluoromethyl.

In the context of this invention a haloalkoxy group designates an alkoxy group as defined herein, which alkoxy group is substituted one or more times with halo. Preferred haloalkoxy groups of the invention include trihalomethoxy, preferably trifluoromethoxy.

In the context of this invention an alkyl-carbonyl group designates an "alkyl-CO— group", wherein alkyl is as defined above. Examples of preferred alkyl-carbonyl groups of the invention include acetyl and propionyl.

In the context of this invention an alkoxy-carbonyl group designates an "alkyl-O—CO—" group, wherein alkyl is as defined above. Examples of preferred alkoxy-carbonyl groups of the invention include the methyl-, ethyl- and propyl-ester group.

In the context of this invention an alkyl-carbonyl-oxy group designates an "alkyl-CO—O—" group, wherein alkyl is as defined above. Examples of preferred alkyl-carbonyl-oxy groups of the invention include acetoxy and propionyloxy.

Pharmaceutically Acceptable Salts

The 8,10-diaza-bicyclo[4.3.1]decane derivative of the invention may be provided in any form suitable for the intended administration. Suitable forms include pharmaceutically (i.e. physiologically) acceptable salts, and pre- or pro-drug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^{2}H$ (deuterium), $^{3}H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), and combinations thereof.

Methods of Producing 8,10-Diaza-bicyclo[4.3.1]decane Derivatives

The 8,10-diaza-bicyclo[4.3.1]decane derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the present invention may be useful for the treatment, prevention or alleviation of a cognitive disorder, learning deficit, memory deficits and dysfunction, Down's syndrome, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, fibromyalgia, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention may be useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the compounds of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the compounds of the invention may be useful for the treatment, prevention or alleviation of a neurodegenerative disorder, transient anoxia, or induced neuro-degeneration.

In a yet more preferred embodiment the compounds of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the compounds of the invention may be useful for the treatment, prevention or alleviation of diabetic neuropathy, schizophrenia, cognitive or attentional deficits related to schizophrenia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the 8,10-diaza-bicyclo[4.3.1]decane derivatives, derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 8,10-diaza-bicyclo[4.3.1]decane derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day iv., and from about 1 µg/kg to about 100 mg/kg/day p.o.

Methods of Therapy

The 8,10-diaza-bicyclo[4.3.1]decane derivatives of the present invention are valuable nicotinic modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of a 8,10-diazabicyclo[4.3.1]decane derivative of the invention.

In a preferred embodiment, the disease, disorder or condition relates to the central nervous system.

The preferred medical indications contemplated according to the invention are those stated above.

It is at present contemplated that suitable dosage ranges are within 0.1 to 1000 milligrams daily, preferably 10 to 500 milligrams daily, and more preferred of from 30 to 100 milligrams daily, dependent as usual upon the exact mode of administration, form in which administered, the indication toward which the administration is directed, the subject involved, the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Method A

10-Methyl-8,10-diaza-bicyclo[4.3.1]decane (Intermediate Compound)

Was prepared according to the preparation of 8-methyl-3,8-diazabicyclo[3.2.1]octane (diethyl mezo-2,5-dibromoadipate to diethyl cis-1-methylpyrrolidine-2,5-dicarboxylate to 3-benzyl-8-methyl-3,8-diazabicyclo[3.2.1]octane-2,4-dione to 3-benzyl-8-methyl-3,8-di-azabicyclo[3.2.1]octane to 8-methyl-3,8-diazabicyclo[3.2.1]octane) by the sequence: 2,7-dibromo-octanedioic acid to 1-methyl-azepane-2,7-dicarboxylic acid dimethyl ester to 8-benzyl-10-methyl-8,10-diaza-bicyclo[4.3.1]decane-7,9-dione to 8-benzyl-10-methyl-8,10-diaza-bicyclo[4.3.1]decane to 10-methyl-8,10-diaza-bicyclo[4.3.1]decane.

References related to the preparation of intermediate compounds: G. Cignarella & G. Nathansohn; *Gazz. Chim. Ital.* 1960 90 1495; S. W. Blackman & R. Baltzly; *J. Org. Chem.* 1960 2750 and G. Cignarella, G. Nathansohn & E Occelli; *J. Org. Chem.* 1960 2747.

Method B

10-Methyl8-(6-phenyl-pyridazin-3-yl)-8,10-diaza-bicyclo [4.3.1]decane Fumaric Acid Salt (Compound B1)

A mixture of 10-methyl-8,10-diaza-bicyclo[4.3.1]decane (0.30 g, 1.94 mmol), 3-chloro-6-phenylpyridazine (0.74 g, 3.89 mmol), N,N-diisopropylamine (0.25 g, 1.94 mmol) and dioxane (10 ml) was stirred at reflux for 4 days. The mixture was evaporated. Aqueous sodium hydroxide (30 ml, 1 M) was added followed by extraction with chloroform (3×30 ml). Chromatography on silica gel with dichloromethane, 10% methanol and 1% aqueous ammonia as solvent gave the title compound as an oil. The corresponding salt was obtained by addition of a diethyl ether and methanol mixture (9:1) saturated with fumaric acid. Yield 0.48 g, 58%. LC-ESI-HRMS of [M+H]+ shows 309.2092 Da. Calc. 309.207921 Da, dev. 4.1 ppm.

8-(6-Iodo-pyridazin-3-yl)-10-methyl-8,10-diaza-bicyclo [4.3.1]decane Free Base (Intermediate Compound)

Was prepared according to Method B from 3,6-diiodopydidazine. LC-ESI-HRMS of [M+H]+ shows 359.0745 Da. Calc. 359.073296 Da, dev. 3.4 ppm.

Method C

10-Methyl-8-(6-phenylethynyl-pyridazin-3-yl)-8,10-diaza -bicyclo[4.3.1]decane Fumaric Acid Salt (Compound C1)

A mixture of 8-(6-iodo-pyridazin-3-yl)-10-methyl-8,10-diaza -bicyclo[4.3.1]-decane (0.43 g, 1.00 mmol), phenylacetylene (0.25 g, 2.4 mmol), N,N-diisopropylamine (0.155 g, 1.2 mmol), copper iodide (23 mg, 0.12 mmol), palladacycle (22.5 mg, 0.024 mmol) and dioxane (20 ml) was stirred at reflux 19 hours. Aqueous sodium hydroxide (30 ml, 1 M) was added followed by evaporation of the dioxane and extraction with chloroform (3×30 ml). Chromatography on silica gel with dichloromethane, 10% methanol and 1% aqueous ammonia as solvent gave the title compound as an oil. The corresponding salt was obtained by addition of a diethyl ether and methanol mixture (9:1) saturated with fumaric acid. Yield 0.22 g, 41%. LC-ESI-HRMS of [M+H]+ shows 333.2083 Da. Calc. 333.207921 Da, dev. 1.1 ppm.

10-Methyl-8-(6-thiophen-3-ylethynyl-pyridazin-3-yl)-8,10-diaza-bicyclo[4.3.1]decane (Compound C2)

Is prepared according to Method C from 3-ethynyl-thiophene.

8-[6-(4-Fluoro-phenylethynyl)-pyridazin-3-yl]-10-methyl-8,10-diaza-bicyclo[4.3.1]decane (Compound C3)

Is prepared according to Method C from 1-ethynyl-4-fluoro-benzene.

8-[6-(4-Methoxy-phenylethynyl)-pyridazin-3-yl]-10-methyl-8,10-diaza-bicyclo[4.3.1]decane (Compound C4)

Is prepared according to Method C from 1-ethynyl-4-methoxy-benzene.

3-[6-(10-Methyl-8,10-diaza-bicyclo[4.3.1]dec-8-yl) -pyridazin-3-ylethynyl]-phenylamine (Compound C5)

Is prepared according to Method C from 3-ethynyl-phenylamine.

N-{3-[6-(10-Methyl-8,10-diaza-bicyclo[4.3.1]dec-8-yl)-pyridazin-3-ylethynyl]-phenyl}-acetamide (Compound C6)

Is prepared according to Method C from N-(3-ethynyl-phenyl)-acetamide.

8-[6-(1H-Indol-5-ylethynyl)-pyridazin-3-yl]-10-methyl-8,10-diaza-bicyclo[4.3.1]decane (Compound C7)

Is prepared according to Method C from 5-ethynyl-1H-indole.

Method D

10-Methyl-8-(6-thiophen-3-yl-pyridazin-3-yl)-8,10-diaza -bicyclo[4.3.1]decane Fumaric Acid Salt (Compound D1)

A mixture of 8-(6-iodo-pyridazin-3-yl)-10-methyl-8,10-diaza -bicyclo[4.3.1]-decane (1.5 g, 4.19 mmol), 3-thiopheneboronic acid (1.62 g, 12.56 mmol), potassium carbonate (1.74 g, 12.56 mmol), palladacycle (78 mg, 0.084 mmol), Pd(PPh3)4 (97 mg, 0.084 mmol), bis(tri-t-butylphosphine)palladium(0) (43 mg, 0.084 mmol), 1,3-propandiol (0.93 g, 12.6 mmol), DME (60 ml) and water (30 ml) was stirred at reflux for 40 h. Aqueous sodium hydroxide (40 ml, 1 M) was added followed by evaporation of the dioxane and extraction with chloroform (3×40 ml). Chromatography on silica gel with dichloromethane, 10% methanol and 1% aqueous ammonia as solvent gave the title compound as an oil. Yield 0.68 g, 52%. The corresponding salt was obtained by addition of a diethyl ether and methanol mixture (9:1) saturated with fumaric acid. LC-ESI -HRMS of [M+H]+ shows 315.1642 Da. Calc. 315.164342 Da, dev. −0.5 ppm 10-Methyl-8-(6-thiophen-2-yl-pyridazin-3-yl)-8,10-diaza -bicyclo[4.3.1]decane Fumaric Acid Salt (Compound D2)

Is prepared according to Method D from 2-thiopheneboronic acid. LC-ESI-HRMS of [M+H]+ shows 315.1628 Da. Calc. 315.164342 Da, dev. −4.9 ppm 8-[6-(3-Methoxy-phenyl)-pyridazin-3-yl]-10-methyl-8,10-diaza-bicyclo[4.3.1]decane (Compound D3)

Is prepared according to Method D from 3-methoxyphenylboronic acid.

8-[6-(4-Methoxy-phenyl)-pyridazin-3-yl]-10-methyl-8,10-diaza-bicyclo[4.3.1]decane (Compound D4)

Is prepared according to Method D from 4-methoxyphenylboronic acid.

10-Methyl-8-(6-naphthalen-2-yl-pyridazin-3-yl)-8,10-diaza-bicyclo[4.3.1]decane (Compound D5)

Is prepared according to Method D from 2-naphthylboronic acid.

8-(6-Benzofuran-2-yl-pyridazin-3-yl)-10-methyl-8,10-diaza-bicyclo[4.3.1]decane (Compound D6)

Is prepared according to Method D from 2-benzofuranylboronic acid.

8-[6-(1H-Indol-5-yl)-pyridazin-3-yl]-10-methyl-8,10-diaza-bicyclo[4.3.1]decane (Compound D7)

Is prepared according to Method D from 1H-Indol-5-yl-boronic acid.

The invention claimed is:

1. A compound represented by Formula I

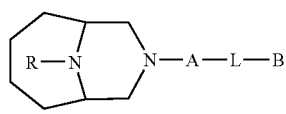 (I)

or a pharmaceutically acceptable salt thereof, wherein

A represents a pyridazinyl group;

L represents a single bond or a linking group —C≡C—;

B represents a phenyl or thienyl group, optionally substituted one or two times with substituents selected from alkyl, cycloalkyl, hydroxyl, alkoxy, halo and trifluoromethyl; and R represents hydrogen or alkyl.

2. The compound of claim 1, or a pharmaceutically acceptable salt thereof, wherein L represents a single bond.

3. The compound of claim 1, or a pharmaceutically acceptable salt thereof, wherein B represents a phenyl or thienyl group.

4. The compound of claim 1, or a pharmaceutically acceptable salt thereof, wherein R represents hydrogen or alkyl.

5. The compound of claim 1, which is

10-Methyl-8-(6-phenyl-pyridazin-3-yl)-8,10-diaza-bicyclo[4.3.1]decane;

10-Methyl-8-(6-phenylethynyl-pyridazin-3 -yl)-8,10-diaza -bicyclo [4.3.1]decane;

10-Methyl-8-(6-thiophen-3-yl-pyridazin-3-yl)-8,10-diaza -bicyclo [4.3.1]decane; or 10-Methyl-8-(6-thiophen-2-yl-pyridazin-3-yl)-8,10-diaza -bicyclo [4.3.1]decane;

or a pharmaceutically acceptable salt thereof.

6. A pharmaceutical composition comprising a therapeutically effective amount of the compound of claim 1, or a pharmaceutically acceptable addition salt thereof, together with at least one pharmaceutically acceptable carrier or diluent.

7. The compound of claim 1, or a pharmaceutically acceptable salt thereof, wherein L represents a linking group —C≡C—.

8. The compound of claim 1, wherein B represents phenyl.

9. The compound of claim 1, or a pharmaceutically acceptable salt thereof, wherein R represents alkyl.

10. The compound of claim 1, or a pharmaceutically acceptable salt thereof, wherein R represents methyl.

* * * * *